(12) United States Patent
Canepa et al.

(10) Patent No.: US 6,984,465 B2
(45) Date of Patent: Jan. 10, 2006

(54) SEAL-LEAK DETECTOR ARRANGEMENT FOR COMPRESSORS AND OTHER EQUIPMENT

(75) Inventors: Richard Thomas Canepa, Plymouth, MN (US); Eivind Stenersen, River Falls, WI (US)

(73) Assignee: Donaldson Company, Inc, Minneapolis, MN (US)

( * ) Notice: Subject to any disclaimer, the term of this patent is extended or adjusted under 35 U.S.C. 154(b) by 359 days.

(21) Appl. No.: 10/236,420

(22) Filed: Sep. 5, 2002

(65) Prior Publication Data

US 2004/0048131 A1    Mar. 11, 2004

(51) Int. Cl.
*H01M 8/04* (2006.01)
*F04B 39/04* (2006.01)

(52) U.S. Cl. .......................... 429/34; 429/12; 137/312; 415/168.1

(58) Field of Classification Search .................. 418/83; 429/12, 30, 34, 3; 137/312; 415/83, 168.1
See application file for complete search history.

(56) References Cited

U.S. PATENT DOCUMENTS

| | | | |
|---|---|---|---|
| 4,159,420 A * | 6/1979 | Tsunoda ................. 250/227.25 |
| 4,659,467 A | 4/1987 | Spearman | |
| 4,733,449 A | 3/1988 | Spearman | |
| 5,047,159 A * | 9/1991 | Zehler ......................... 508/214 |
| 5,890,881 A | 4/1999 | Adeff | |
| 6,050,130 A * | 4/2000 | Kramer ...................... 73/24.01 |

| | | |
|---|---|---|
| 6,432,177 B1 | 8/2002 | Dallas et al. |
| 2002/0106294 A1 | 8/2002 | Nakane et al. |
| 2002/0157359 A1 | 10/2002 | Stenersen et al. |

FOREIGN PATENT DOCUMENTS

| | | | |
|---|---|---|---|
| EP | 753722 A2 | * | 1/1997 |
| EP | 1 118 770 | | 7/2001 |
| EP | 1 118 770 A1 | | 7/2001 |
| FR | 2569780 | | 3/1986 |
| GB | 959461 | | 6/1964 |
| JP | 08078035 A | * | 3/1996 |
| JP | 2001332285 A | * | 11/2001 |

OTHER PUBLICATIONS

Machine translation of JP 2001-332285-A from JPO internet site.*
"Fuel Cell Handbook", 5th ed., US Department of Energy, Oct. 2000 pp. 1-1 through 1-5, 1-11, 1-12, 1-29 and 1-35.*

* cited by examiner

Primary Examiner—Gregg Cantelmo
(74) Attorney, Agent, or Firm—Merchant & Gould P.C.

(57) ABSTRACT

An early warning system for equipment or processes which can be permanently or temporarily damaged by contaminants coming from air moving equipment, such as a compressor, positioned upstream of air flowing through the equipment. The present invention provides a seal-leak detection arrangement that, when incorporated into air moving equipment, monitors the air passing through the air moving equipment for the presence of contaminants such as lubricant oil, which could damage the equipment downstream. At least one sensor is positioned downstream of a contaminant retaining seal within the air moving equipment. The seal-leak detection arrangement is particular useful when incorporated into systems upstream of a fuel cell.

15 Claims, 2 Drawing Sheets

SEAL-LEAK DETECTOR ARRANGEMENT FOR COMPRESSORS AND OTHER EQUIPMENT

BACKGROUND OF THE INVENTION

The present invention is directed to equipment and methods for detecting seal failure for air moving equipment such as compressors. More specifically, this invention is directed to sensors and their placement for detecting oil leakage into an air or gas stream downstream from the air moving equipment.

Air compressors, fans, blowers, turbo-chargers and other air moving equipment are commonly used to provide necessary oxygen or air flow to power-producing equipment or other equipment that functions as a result of the air flow. Examples of such equipment include engines, motors, and low temperature catalytic reactions, such as fuel cells. For many applications where air moving equipment such as listed above is used, the quality or purity of the air provided to downstream equipment is not critical. However, there are a number of applications such as for certain kinds of power-producing equipment, in which any contaminants, such as particulates and chemical fumes within the air stream, must be kept low in order to have the power-producing equipment function properly and efficiently. A fuel cell is one type of power-producing equipment whose efficiency and operation can be detrimentally affected, even inhibited, by certain types of airborne contaminants.

A fuel cell has an anode and a cathode, and power is generated through a catalytic reaction. One common type of fuel cell is a hydrogen fuel cell, in which a hydrogen fuel source is directed to the anode, where the hydrogen electrons are freed, leaving positively charged ions. The freed electrons travel through an external circuit to the cathode and, in the process, provide an electrical current that can be used as a power source for external electrical circuits. The positively charged ions diffuse through the fuel cell electrolyte and to the cathode where the ions combine with the electrons and oxygen to form water and carbon dioxide, by-products of the process. To speed the cathodic reaction, a catalyst is often used.

Chemical contaminants present in either the hydrogen source or the oxygen source can inhibit the operation of the fuel cell. In fuel cell systems, the ambient air stream containing the necessary oxygen is usually compressed and/or accelerated by air moving equipment such as air compressors, flans, blowers, turbo chargers, or the like, before reaching the cathode, in order to provide the required amount of oxygen to the cathode. U.S. Pat. No. 6,432,177 (Dallas et al.), U.S. patent application Ser. No. 09/832,715, filed Apr. 11, 2001, Ser. No. 09/879,441, filed Jun. 12, 2001 and Ser. No. 10/122,647, filed Apr. 10, 2002 describe systems for removing both chemical and particulate contaminants form the air stream that provides the oxygen to a fuel cell. However, the systems described in these applications are primarily directed to removing contaminants from the air stream prior to the air stream passing through the air moving equipment. These systems are not arranged to remove contaminants that might be generated on produced by the air moving equipment.

What is needed is an arrangement to inhibit, preferably eliminate, contamination of the air stream by the air moving equipment itself and to provide for timely shutdown of the fuel cell system in the event of excess contamination of the air stream.

SUMMARY OF THE INVENTION

The present invention provides an early warning system that can be used for any equipment or process which could be detrimentally affected by the presence of contaminants in the air stream or other gaseous stream. The early warning system of this invention is particularly suitable for delicate power-producing equipment which can be permanently or temporarily damaged by contaminants coming from air moving equipment positioned upstream of air or other gas flowing through the power-producing equipment. The system of this invention is also suitable for other equipment where the cleanliness of the gas stream is important such as a paint sprayer or tools.

The present invention provides a seal-leak detection arrangement that, when incorporated into air moving equipment, monitors the gas passing through the air moving equipment for contaminants such as hydrocarbons, for example lubricant oil, or silicone, which could damage the power-producing equipment or other equipment or processes positioned downstream of the air moving equipment. Sensors are positioned within the air moving equipment to monitor and warn of leaks from within the air moving equipment, leaks such as lubricant oil leaks.

In one particular embodiment, this invention is directed to air moving equipment that has an inlet and an outlet, and an air flow path connecting the inlet to the outlet. The air moving equipment also has a contamination source. A seal-leak detection system is positioned within the air flow path downstream of the contamination source and upstream of the outlet. Usually, the contamination source is a lubricant source, such as bearing lubricant.

In another particular embodiment, this invention is directed to a system that includes air moving equipment, the equipment having an inlet, an outlet, and an air flow path connecting the inlet to the outlet, and a contamination source. A seal-leak detection system is positioned in the equipment within the air flow path downstream of the contamination source and upstream of the outlet. The system includes a fuel cell having an oxidant inlet for receiving air from the air moving equipment outlet.

DETAILED DESCRIPTION

In a preferred embodiment of the invention the seal-leak detector arrangements of the present invention are described as incorporated into air handling or air moving equipment, such as a compressor, which, when the compressor is incorporated into a system, protects the equipment downstream of the compressor from contamination caused by lubrication oil or other contaminants that may pass through or be produced by the air handling equipment. Compressors and other air moving equipment include various types of seals to contain lubricant oil around the bearings. Due to normal usage of the equipment over time, these seals wear and/or breakdown, resulting in leakage.

Although the terms "air moving equipment", "air handling", "air stream", and the like are used throughout this specification, it is understood that other gaseous streams, such as oxygen-enriched air, pure oxygen, carbon dioxide, hydrogen, helium, nitrogen, argon, mixes, or any other gaseous material may be used with the seal-leak detector arrangements of the present invention.

Figure 1:
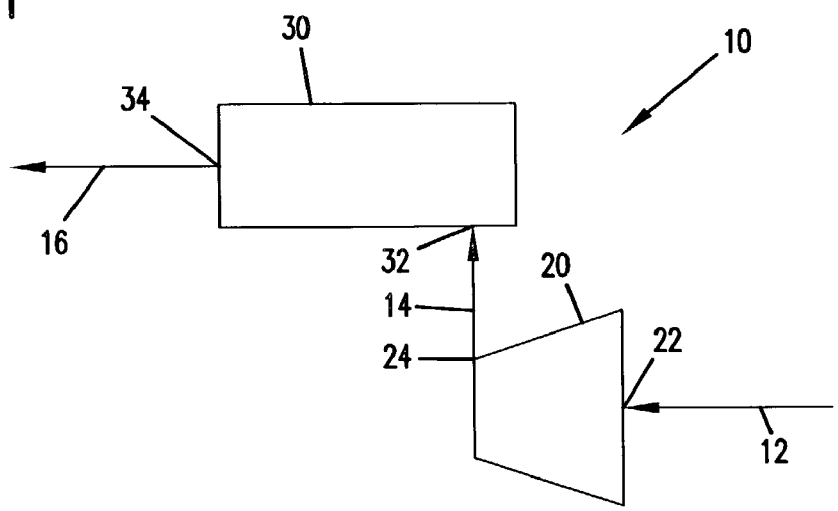
FIG. 1 is a schematic view of a system comprising air handling equipment.

Referring to FIG. 1, system 10 is schematically illustrated as including air handling equipment 20 and downstream equipment 30. Incoming air stream 12, typically ambient air, enters air handling equipment 20 at inlet 22 and exits at outlet 24.

Examples of suitable air moving equipment include compressors, fans, blowers, turbo-chargers, expanders, and vacuum pumps. Specific examples of various types of compressors include rotary compressors such as rotary lobe, rotary screw, rotary scroll, rotary vane, rotary sliding vane, reciprocating compressors, centrifugal (both multistage and single stage), air cooled, water cooled, single stage, double acting, multiple stage, and high pressure compressors. An example is one specific compressor type that is particularly useful in fuel cell applications is a "Lysholm" twin screw compressor, which is available from Opcon Autorotor AB of Sweden.

Air stream 14 from outlet 24 progresses to inlet 32 of equipment 30. Equipment 30 can be any equipment that uses air or another gaseous feed stream to operate, such as to produce power, and which requires the air stream to be relatively free of contaminants that maybe produced by the air moving equipment 20. Examples of power-producing equipment that can be used in system 10 include thermal engines, such as spark ignition or compression ignition, electric motors, steam engines, and fuel cells. Examples of other equipment that would benefit from a seal-leak detection arrangement of the present invention include paint sprayers, clean room ventilation systems, compressed air lines that power to tools, carbonation gas for beverages, and medical air.

Equipment 30 is generally of the type that can be damaged by the presence of lubricant oil, which is typically a hydrocarbon-based material or silicone-based synthetic oil, or which could alternately or additionally be used in an application wherein the air stream passing there through could cause damage to an article or process to which the air stream is subsequently applied. For example, the catalyst and/or electrolyte of a fuel cell can be permanently damaged by contact with hydrocarbons, silicone or sulfur, whether in solid particulate, liquid, or vapor form. The seal-leak detection arrangement of the present invention minimizes, and preferably eliminates, the opportunity for leaking oil or other contaminants originating from air moving equipment 20 to contaminate the air stream passing through the air moving equipment 20 to such an extent that such contamination would be harmful to equipment 30 or to the downstream use-application being serviced by the equipment 30. The seal-leak detection arrangement monitors and warns of any leaks, thus providing an early warning system to avoid costly damage to power-producing equipment 30 or other processes downstream of air moving equipment 20.

Air moving equipment 20 includes a seal-leak detection arrangement of the present invention. In a preferred application of the invention, the seal-leak detection arrangement is designed and constructed to detect leakage of lubrication oil through the seals generally present in air moving equipment 20 such as compressors and blowers. If any oil is detected, system 10 can be shut down before the escaping oil causes, either temporary or permanent damage, to equipment 30 or otherwise raises to an unacceptable level in the air stream supplied to downstream equipment 30.

Air moving equipment 20 generally includes a rotatable shaft which mounts a plurality of blades or vanes for moving air from the inlet to the outlet of the air moving equipment. Such shaft is typically mounted in or surrounded by the path of the air being processed by air moving equipment 20.

Figure 2:
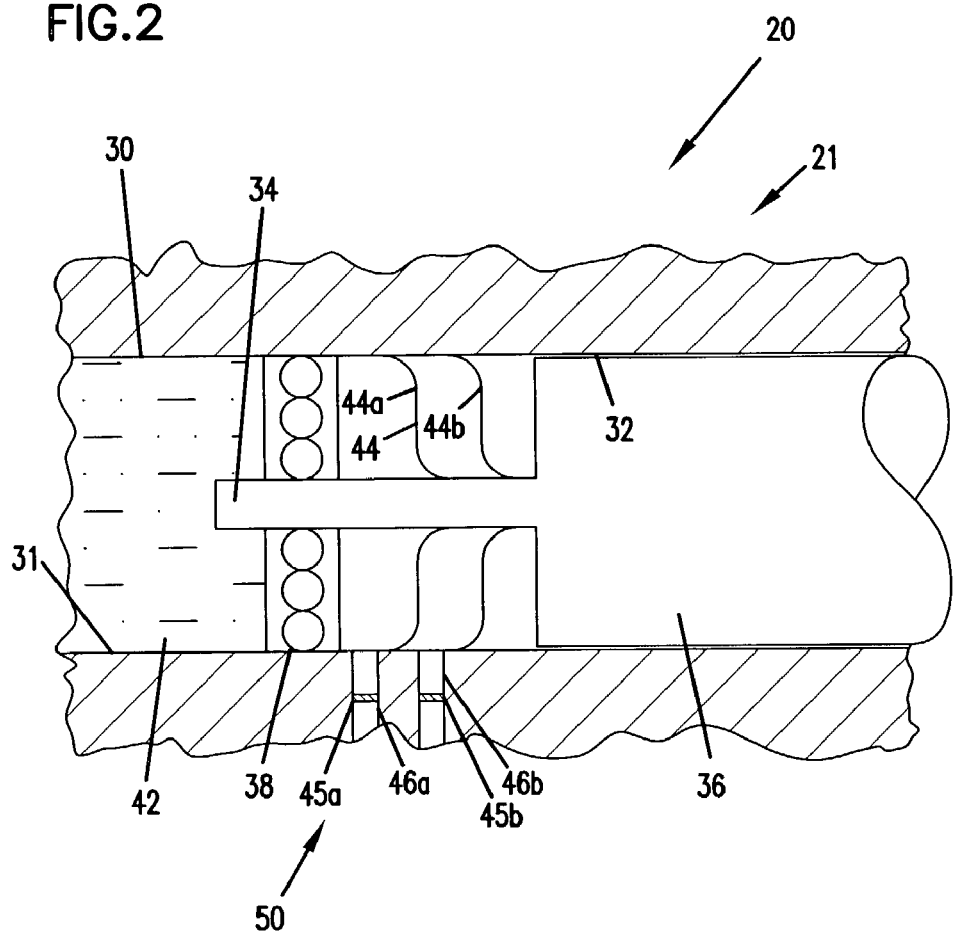
FIG. 2 is schematic partial view of a first embodiment of a seal-leak detection arrangement usable with air handling equipment such as shown in FIG. 1.

Referring now to FIG. 2, a first embodiment of a seal-leak detection arrangement 50 in a partial view of air moving equipment 20 is illustrated. In this embodiment, air handling equipment 20 represents a twin-screw air compressor 21, having a body or housing 30 defining a bore 32, which houses a rotatable shaft 34 connected to lobe 36. Shaft 34 is supported for rotation by bearings mounted within bore 32, one set of which is illustrated at 38. Bearings 38 are engulfed in lubrication oil 42, which is retained in oil chamber 31 also defined by housing bore 32. Lubrication oil 42 decreases frictional wear on bearings 38, shaft 34, and on timing gears (not shown), and decreases the operating temperature thereof. Bearing 38 is secured within bore 32 in a manner designated to retain oil 42 within oil chamber 31. Secondary oil seals, flexible seals 44, slidably engage rotating shaft 34 for providing additional liquid-tight seals between bore 32 and shaft 34, to retain any oil 42 leaking past bearing 38 within bore chamber. Seals 44 may commonly also be referred to as oil wiper rings or seals. In the embodiment shown, two flexible seals 44a, 44b are present. These various features of air compressor 21 are conventional and are well known in the field of compressors and other air moving equipment. In accordance with the present invention, a seal-leak detection system 50 is incorporated into compressor 21, in particular in relation to seals 44, to detect any oil 42 that may progress past bearing 38 and seals 44a, 44b. The seal-leak detection system 50 provides an early warning system intended to prevent damage to equipment 30 or to process being preformed by equipment 30, caused by oil 42 leaking through the bearing seal or worn or damaged seals 44a.

In particular, seal-leak detection system 50 includes sensors, in this embodiment, a first sensor 45a and a second sensor 45b, each positioned in a hole or bore 46a, 46b, respectively, formed within housing 30 the downstream their respectively monitored seals. The diameters of holes 46a, 46b should be sized to operatively accept sensor 45a, 45b therein (for example, 6 mm diameter). Hole 46a, 46b would preferably be configured to pass through housing 30 and into the chamber where leaking oil would be present, such that sensors mounted within the holes could be positioned therein from outside of housing 30. Sensors 45a, 45b can be threaded or merely snap-fit into holes 46a, 46b. Preferably, each of holes 46a, 46b is at a low spot in housing 30 with respect to bore 32. First hole 46a with first sensor 45a is positioned between bearing 38 and first seal 44a, and second hole 46b with second sensor 45b is positioned between first seal 44a and second seal 44b. Each of sensors 45a, 45b monitors for and warns of the presence of oil 42. First sensor 45a is a primary sensor that monitors for the presence of any oil that may have leaked past bearing 38. Second sensor 45b is a secondary sensor that monitors for the presence of any oil that may have leaked past both bearing 38 and first seal 44a. Data confirming the detection of oil by either sensor 45a, 45b can be used to shut down the system, thereby avoiding permanent damage to equipment 30. In an alternate configuration, confirmation of a leak by first sensor 45a can be a warning that bearing 38 is beginning to leak and may need replacement. However, if no oil preserve is detected by sensor 45b, seal 44a may not be sufficiently worn or damaged to warrant immediate shut down and replacement. Subsequent sensing of oil by second sensor 45b can then be used to automatically shut down the system.

As stated above, sensors 45a, 45b are configured to detect the presence of liquid lubricant oil 42. Additionally or alternatively, sensors 45a, 45b can be configured to detect the presence of, for example, molecular amounts of hydrocarbons, silicone, sulfur, or other materials that are components of oil 42. Examples of suitable sensors for sensing either liquid material or molecular amounts include those that operate by refraction and reflection. A reflective sensor 45a, 45b operates by monitoring reflectance of a beam of light emitted into housing 30 where lubricant oil may leak. The presence of oil or other contaminant within the light path will affect the reflectance reading. One example of a suitable reflective sensor is Part FU67G, available from Keyenes.

The sensors are typically operably connected, such as by optical fibers or cables, to other signal processing equipment, such as to an amplifier. An example of a suitable amplifier for use in conjunction with a FU67G sensor is amplifier Part FSM1, also from Keyenes. If desired, multiple sensors can be connected in series or in parallel. Typically, a second amplifier would be used for a second sensor. An example of a suitable amplifier for use in a series connected sensor configuration using a first FSM1 amplifier is a Part FSM2 amplifier, also available from Keyenes.

Figure 3:
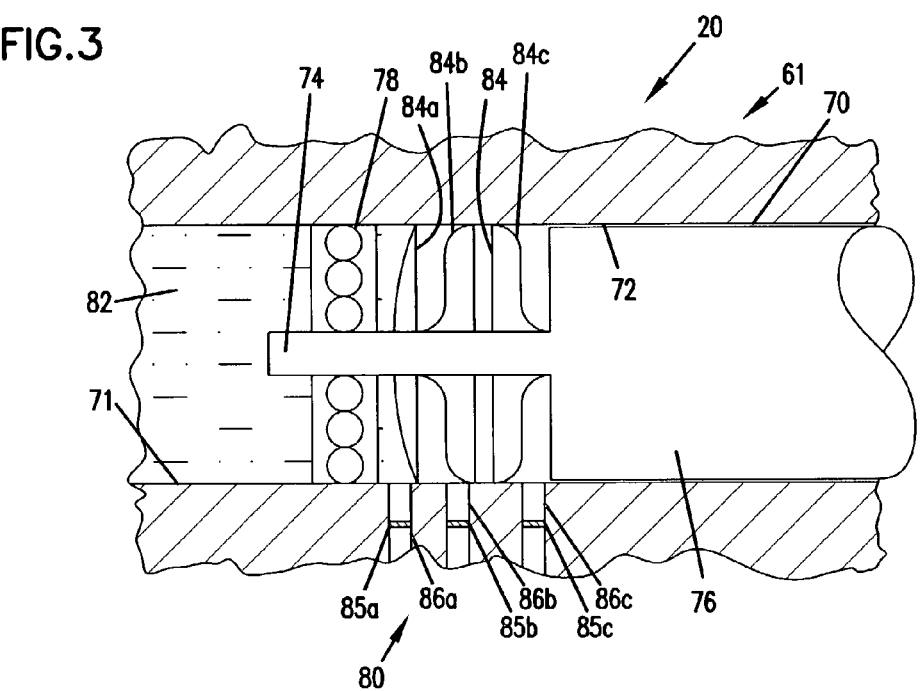
FIG. 3 is a schematic partial view of a second embodiment of a seal-leak detection arrangement usable with air handling equipment such as shown in FIG. 1.

A second embodiment of a seal-leak detector assembly is illustrated in FIG. 3. In this embodiment, air equipment 20 represents an air compressor 61, having a body or housing 70 defining a bore 72, which houses a cylindrical, rotatable shaft 74 connected to cylindrical lobe 76. Shaft 74 and lobe 76 are mounted for rotation within bore 72 by mean of bearings, one set of which is illustrated at 78. Bearings 78 are engulfed by lubrication oil 82 retained in oil chamber 71 by a series of inflexible seals 84. In the embodiment shown, three seals 84a, 84b, 84c are illustrated ad appear to be similar to vanes. The left most seal 84 is the primary seal for retaining oil 82 within oil chamber 71. If oil leaks past first seal 84a, second seal 84b is provided to interrupt any oil leaking past first seal 84a. Similarly, third seal 84c is provided to interrupt any oil leaking part second seal 84b. A seal-leak detection system 80 is used with seals 84a, 84b, 84c to detect if any oil 82 progresses past seals 84a, 84b, 84c. In particular, seal-leak detection system 80 includes a series of sensors 85 positioned within drain holes in housing 70. That is, a first sensor 85a is positioned in a hole 86a between seals 84a and 84b, a second sensor 85b is positioned in a hole 86b between seals 84b and 84c, and a third sensor 85c is positioned downstream of seal 84c in a hole 86c.

Similar to sensors 45a, 45b of FIG. 2, sensors 85a, 85b, 85c are configured to detect the presence of any lubricant oil that may have leaked past seals 84 and that could potentially damage downstream equipment or processes.

It is understood that seal-leak detection arrangements 50, 80 can be incorporated into any type of air moving or air handling equipment for which leaking lubricating oil could pose a threat to downstream equipment or processes. Additionally, seal-leak detection arrangement 50, 80 can be used on air moving or aid handling equipment used with any equipment or process which could be detrimentally affected by the presence of lubrication oil contamination.

Figure 4:
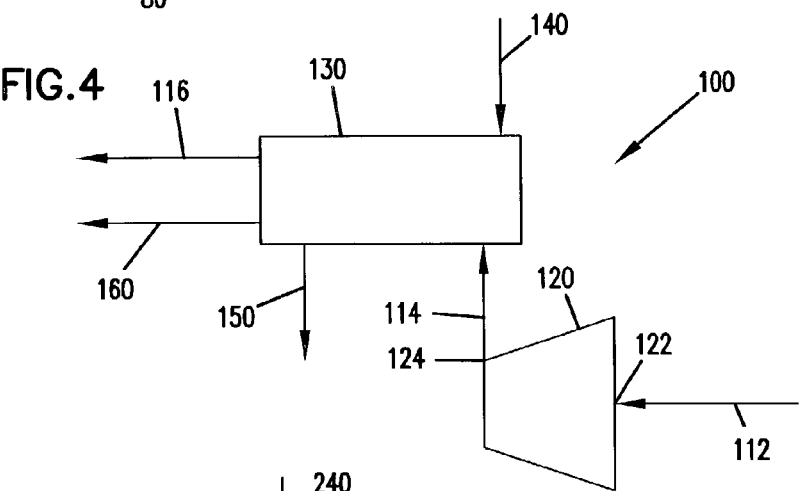
FIG. 4 is a schematic partial view of a fuel cell system comprising air handling equipment and a fuel cell.
Figure 5:
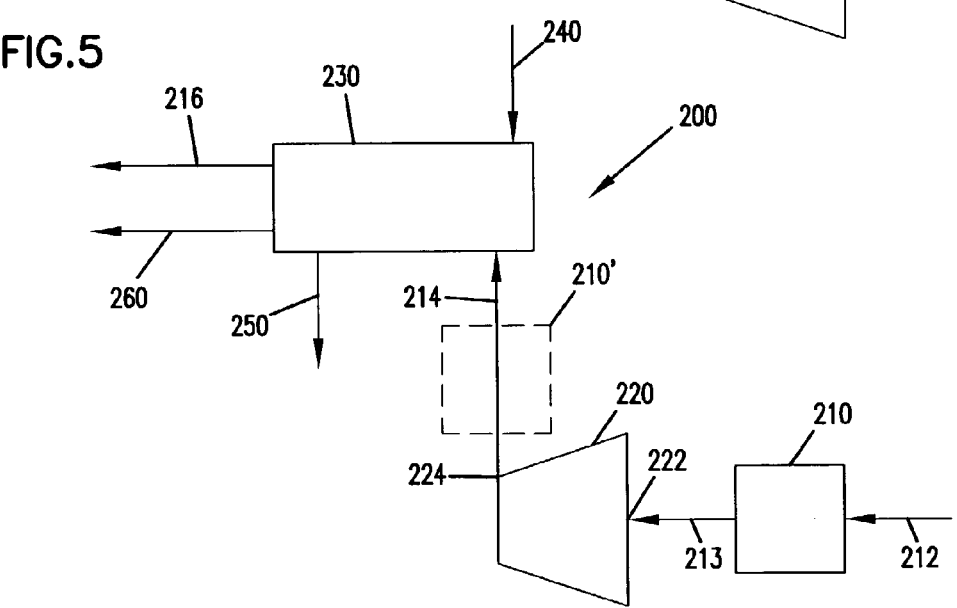
FIG. 5 is a schematic partial view of a fuel cell system comprising a filter, air handling equipment, and a fuel cell.

Referring to FIGS. 4 and 5, systems 100 and 200, respectively, utilize air moving equipment 120, 220 which respectively incorporate an embodiment of the seal-leak detection arrangement of the types described above.

System 100 of FIG. 4 has air stream 112 entering air moving equipment 120 at inlet 122 and exiting as air stream 114 via outlet 124. Air stream 114 enters power-producing equipment 130, which is, in the preferred embodiment, a particular fuel cell 130.

Fuel cell 130 is an electrochemical device that efficiently converts a fuel's chemical energy to electrical energy. Fuel cell 130 chemically combines a fuel and oxidant without burning, thereby eliminating many inefficiencies and most pollution of traditional combustion power systems. Fuel cell 130 operates in principle much like a battery. However, unlike a battery, fuel cell 130 does not run down or require recharging; it will continue to produce energy in the form of electricity and heat as long as fuel and oxygen is supplied to it.

In general, fuel cell 130 consists of two electrodes (an anode and a cathode) sandwiched around an electrolyte. In a preferred configuration, fuel cell 130 is a PEM type, low temperature fuel cell. For a PEM fuel cell, hydrogen and oxygen are passed over the anode and cathode electrodes, respectively, in a manner that generates a voltage between the electrodes, creating electricity, and producing water and carbon dioxide as the primary by-products. The hydrogen fuel is supplied to the anode of the fuel cell. Some fuel cells consume hydrogen directly, while others use a fuel reformer to extract the hydrogen from, for example, a hydrocarbon fuel such as natural gas, methanol, ethanol, or gasoline. Oxygen enters the fuel cell at the cathode. The oxygen can be supplied in purified form or can come directly from atmospheric air.

Fuel cell 130 uses a catalyst to cause the hydrogen atom to split into a proton and an electron, each of which takes a different path to the cathode. The protons pass through the electrolyte. The electrons create a useful electric current that can be used as an energy source, before returning to the anode where they are reunited with the hydrogen protons and the oxygen to form water.

Fuel cell 130, and other fuel cells, are generally characterized by the electrolyte material which is sandwiched between the cathode and anode, and which serves as a bridge for ion exchange. There are five main known types of fuel cells. Alkaline fuel cells (AFCs) contain a liquid alkaline electrolyte and have been used primarily in space mission applications. Proton exchange membrane fuel cells (PEM or PEMFCs) contain a solid polymer electrolyte. Their low temperature operation, high power density with the ability to vary their output quickly to meet shifts in power demand make their use ideal for both mobile and stationary applications, such as powering vehicles or buildings. Phosphoric acid fuel cells (PAFCs) utilize a phosphoric acid electrolyte and are currently used for commercial power generation. Molten carbonate fuel cells (MCFCs) contain a carbonate salt electrolyte, which becomes molten at the operating temperature of about 650° C. Solid oxide fuel cells (SOFCs) use a ceramic electrolyte material and operate up to about 1000° C. Both the MCFCs and the SOFCs can use carbon monoxide as fuel.

The primary types of known fuel cell configurations are discussed above. They all have the common characteristics briefly discussed, but vary in operating temperatures and efficiency of operation. A hydrogen fuel source is directed to the anode, where the hydrogen electrons are freed, leaving positively charged ions. The freed electrons travel through an external circuit to the cathode and, in the process, provide an electrical current that can be used as a power source for external electrical circuits. The positively charged ions diffuse through the fuel cell electrolyte to the cathode where the ions combine with the electrons and oxygen to form water and carbon dioxide, by-products of the process. To speed the cathodic reaction, a catalyst is often used. Examples of catalysts often used in the fuel cell reaction include nickel, platinum, palladium, cobalt, cesium, neodymium, and other rare earth metals.

The proton exchange membrane (PEM) type of fuel cell is a popular fuel cell configuration for use in powering vehicles due to its low temperature operation, high power density and ability to quickly vary its power output to meet shifts in power demand. The PEM fuel cell is often simply referred to as a "low temperature fuel cell" because of its low operation temperature, typically about 70 to 100° C., sometimes as high as 200° C. Fuel cell 130 is preferably of the PEM, low temperature configuration, or the SOFC (solid oxide) configuration. The construction and operation of fuel cells, in general, is well known. Various fuel cells are commercially available from, for example, Ballard Power Systems, Inc. of Vancouver, Canada; United Technology Corp. (UTC), of Connecticut; Proton Energy Systems, Inc. of Rocky Hill, Conn.; American Fuel Cell Corp. of Massachusetts; Siemans AG of Erlangen, Germany; Global Alternative Propulsion Center of General Motors of Detroit, Mich.; and Toyota Motor Corporation of Japan. Individual fuel cells, each having an anode, cathode, and electrolyte, are configured into "stacks" to provide the desired amount of external power. It will be recognized that the principles of this invention will benefit the operation of generally any fuel cell configuration.

The threshold levels of contaminants that are acceptable by various fuel cells are dependent on the design of the fuel cell. For example, hydrocarbons (methane and heavier), ammonia, sulfur dioxide, carbon monoxide, silicones, and the like, are known to occupy space on the catalyst and inactivate the sites to reaction. Thus, these contaminants need to be removed prior to their entering the reactive area of the fuel cell.

The exact threshold level of contamination, and types of contaminants that are acceptable will vary depending on the catalyst used, the operating conditions, and the catalytic process efficiency requirements. The seal-leak detection arrangement of the present invention shuts down the incoming air stream before the contaminants have an opportunity to damage the catalyst, electrolyte, or other part of the fuel cell.

Referring again to FIG. 4, air stream 114, having passed through air moving equipment 120 having the seal-leak detection arrangement of an embodiment of the present invention therein, provides a supply of oxygen to fuel cell 130. Hydrogen fuel enters fuel cell 130 as hydrogen stream 140. Fuel cell 130 converts hydrogen and oxygen to provide electric power 160 and water 150 as a by-product. The air stream exists fuel cell 130 as outlet stream 116.

Referring to FIG. 5, system 200 is similar to system 100 of FIG. 4, except that system 200 includes a filter assembly through which the air stream passes prior to entering the air moving equipment. Specifically, system 200 includes filter assembly 210 into which the air stream enters as stream 212 and exits as stream 213.

Filter assembly 210 provides filtration to the incoming air stream 212 to provide a purified air stream 213 or oxidant to the intake side of fuel cell 230. Filter assembly 210 captures and retains particulate and/or chemical contaminants that can harm the combustion or catalytic process, the electrolyte, or both. Filter assembly 210 can also provide sound suppression or attenuation for any noise emanating from air moving equipment 220, such as a compressor, that may be operatively connected with fuel cell 230.

A first example of filter assembly 210 has a housing and a filter element in the housing. The housing has an inlet and an outlet, the inlet receiving dirty air (i.e., air stream 212) into the filter assembly, and the outlet providing clean filtered air (i.e., air stream 213) from filter assembly 210. The filter element has a particulate filter portion constructed and arranged to remove physical or particulate contaminants from air stream 212 and may have a chemical filter portion constructed and arranged to remove chemical contaminants from air stream 212. The filter assembly also has a sound suppression element, such as a resonator, sonic choke, full choke, sound adsorbent material, that attenuates or otherwise reduces sound by at least 3 dB at one meter, preferably by at least 6 dB. See, for example, pending U.S. patent application Ser. No. 09/832,715, filed Apr. 11, 2001 which is incorporated herein by reference.

A second example of filter assembly 210 has a filter element comprising a sound suppression element, a particulate filter portion, and a chemical filter portion. The sound suppression element is constructed and arranged to provide broadband sound attenuation of at least 6 dB at one meter. The particulate filter portion is constructed and arranged to remove particulate contaminants from dirty air (i.e., air stream 212) entering the filter element, and the particulate filter portion is positioned radially adjacent the sound suppression element. The chemical filter portion is provided to remove chemical contaminants from the dirty air. In some configurations, the particulate filter portion can be configured to provide straight-through flow. See, for example, pending U.S. patent application Ser. No. 09/879,441 filed Jun. 12, 2001, which is incorporated herein by reference.

It is understood that any other arrangements of filter assembly 210 can be used. Additional information regarding filter assembly 210, and various alternate embodiments, are described in U.S. Pat. No. 6,432,177 and U.S. patent application Ser. No. 10/122,647, filed Apr. 10, 2002, both incorporated herein by reference.

Referring to the portion of system 200 downstream of filter assembly 210, filter air steam 213 from filter assembly 210 enters air moving equipment 220 via inlet 222. After being processed by air moving equipment 220 having the seal-leak detection arrangement of the present invention, the air exits via outlet 224 as stream 214. In some system configurations, it may be desired to include a filter assembly downstream of compressor 220 and upstream of fuel cell 230. Such an "exhaust" filter assembly illustrated in phantom in FIG. 5 as exhaust filter assembly 210', can include any of a particulate filter portion, a chemical filter portion, and a sound suppression element. Examples of exhaust filter assemblies are disclosed in U.S. patent applications Ser. Nos. 09/832,715, 09/879,441, and 10/122,697. Air stream 214 provides a supply of oxygen to fuel cell 230. Hydrogen fuel enters fuel cell 230 as hydrogen stream 240. Fuel cell 230 converts hydrogen and oxygen to provide electric power 260 and water 250 as a byproduct. The air stream exists fuel cell 230 as outlet stream 216.

The above specification, examples and data provide a complete description of the manufacture and use of the composition of the invention. Since many embodiments of the invention can be made without departing from the spirit and scope of the invention, the invention resides in the claims hereinafter appended.

What is claimed:

1. Air moving equipment, being a twin screw compressor or a rotary compressor, the air moving equipment comprising:
   (a) an inlet and an outlet;
   (b) an air flow path connecting the inlet to the outlet;
   (c) a hydrocarbon or silicone contamination source; and
   (d) a seal-leak detection system comprising a sensor to detect the presence of hydrocarbon or silicone, the sensor positioned within the air flow path and in contact with the air flow downstream of the contamination source and upstream of the outlet.

2. The air moving equipment according to claim 1, wherein the contamination source is a lubricant.

3. The air moving equipment according to claim 2, wherein the lubricant comprises silicone.

4. The air moving equipment according to claim 1, wherein the sensor is positioned downstream of an internal seal of the air moving equipment.

5. The air moving equipment according to claim 4, wherein the sensor is constructed and arranged to sense contamination by refraction.

6. The air moving equipment according to claim 4, wherein the sensor is constructed and arranged to sense contamination by reflection.

7. The air moving equipment according to claim 1, wherein the seal-leak detection system comprises two sensors positioned within the air flow pat and in contact with the air flow downstream of the contamination source and upstream of the outlet.

8. A system comprising:
   (a) air moving equipment selected from the group of a twin screw compressor and a rotary compressor, the air moving equipment comprising:
      (i) an inlet, an outlet, and an air flow path connecting the inlet to the outlet;
      (ii) a hydrocarbon or silicone contamination source; and
      (iii) a seal-leak detection system comprising a sensor to detect the presence of hydrocarbon or silicone, the sensor positioned within the air flow path and in contact with the air flow downstream of the contamination source and upstream of the outlet; and
   (b) a fuel cell having an oxidant inlet for receiving air from the air moving equipment outlet.

9. The system according to claim 8, wherein the fuel cell is a PEM fuel cell.

10. The system according to claim 8, wherein the fuel cell is a solid oxide fuel cell.

11. The system according to claim 8, wherein the seal-leak detection system comprises a sensor positioned downstream of an internal seal of the air moving equipment.

12. The system according to claim 11, wherein the sensor is constructed and arranged to sense contamination by refraction.

13. The system according to claim 11, wherein the sensor is constructed and arranged to sense contamination by reflection.

14. The system according to claim 8, wherein the contamination source is a lubricant from around a bearing in the air moving equipment.

15. The system according to claim 8, wherein the seal-leak detection system comprises two sensors positioned within the air flow path and in contact with the air flow downstream of the contamination source and upstream of the outlet.

* * * * *